United States Patent [19]
Barber

[11] 3,965,509
[45] June 29, 1976

[54] LEAF CUTTER BEE LARVAE EXTRACTING DEVICE

[76] Inventor: Theodore C. Barber, P.O. Box 5, Orovada, Nev. 89425

[22] Filed: July 21, 1975

[21] Appl. No.: 597,721

Related U.S. Application Data

[63] Continuation of Ser. No. 574,079, May 2, 1975, abandoned.

[52] U.S. Cl.................................................. 6/12 A
[51] Int. Cl.$^2$.......................................... A01K 51/00
[58] Field of Search.................. 6/12 R, 12 A, 12 M

[56] References Cited
UNITED STATES PATENTS

| | | | |
|---|---|---|---|
| 2,272,808 | 2/1942 | McFadyen | 6/12 A |
| 2,448,986 | 9/1948 | Ladwig | 6/12 A |
| 3,293,672 | 12/1966 | Gregersen | 6/12 A |
| 3,388,409 | 6/1968 | Hettrick | 6/12 A |
| 3,609,780 | 10/1971 | Cowen | 6/12 A |

*Primary Examiner*—Louis G. Mancene
*Assistant Examiner*—Jack Q. Lever
*Attorney, Agent, or Firm*—John W. Kraft; Charles L. Kraft, II

[57] ABSTRACT

The apparatus for cleaning bee culture frames of the type having slots for frames, which are formed into blocks by aligning the frames, comprises a suitable framework, an in-feed ramp, a board-breaker assembly, and a board-cleaning assembly. The infeed ramp carries the blocks to a vertically disposed channel provided on the framework, the channel controlling forward movement of the block on the ramp and conducting frames separated from the block downwardly in the apparatus. The board-breaker assembly comprises at least a blade reciprocating vertically in a channel disposed parallelly to the frames with the contact face of the blade being disposed at a predetermined position to operate adjacently disposed frames in the block, and frame-cleaning teeth which interdigitate with slots of the frame. The board-cleaning assembly is disposed distally below the board-breaker assembly along the vertical channel, the cleaning assembly removing foreign material, larvae and the like from the frames, and a reassembly and off-feed assembly including an off-feed conveyor disposed below the cleaning assembly at the lowermost portion of the channels, the channels being provided with elements for rectilinearly aligning the frames into the block. The apparatus may also include a larvae separator.

9 Claims, 7 Drawing Figures

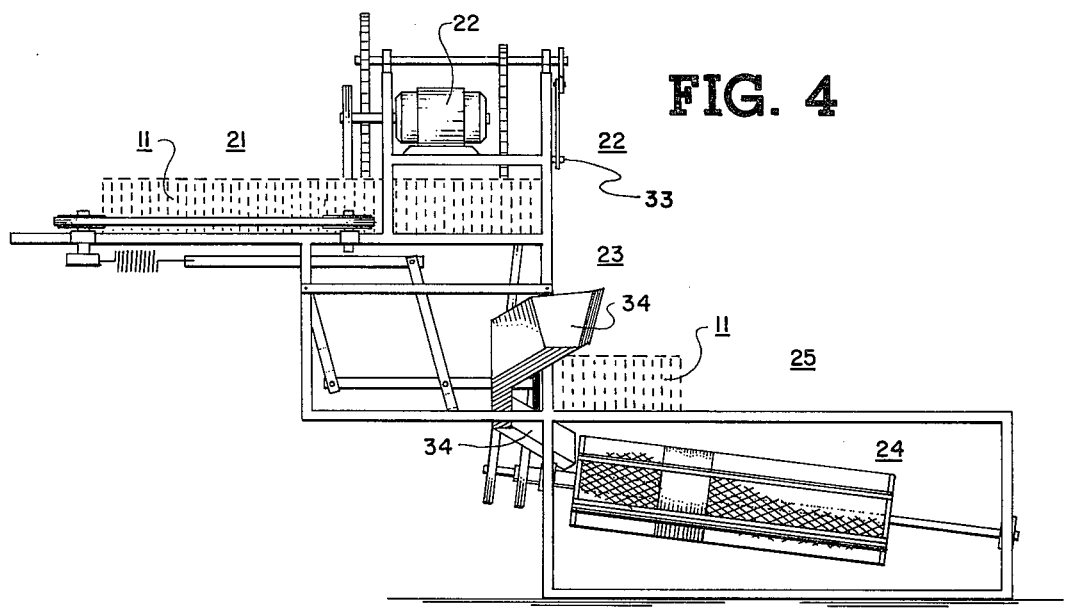
FIG. 4
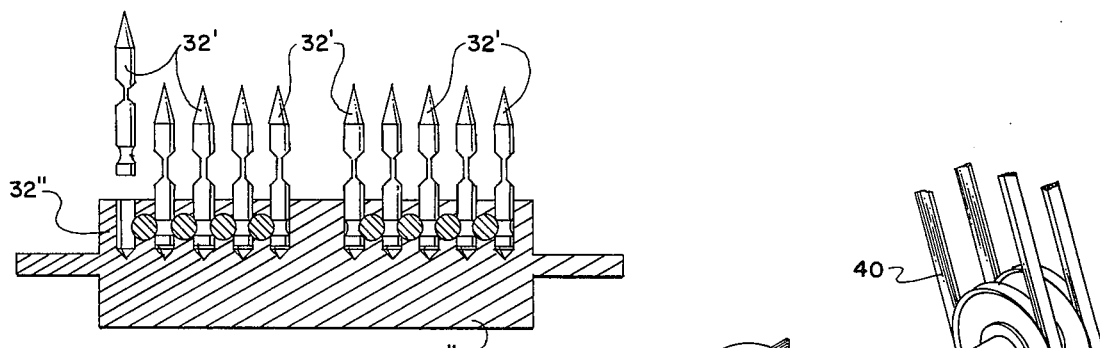
FIG. 5
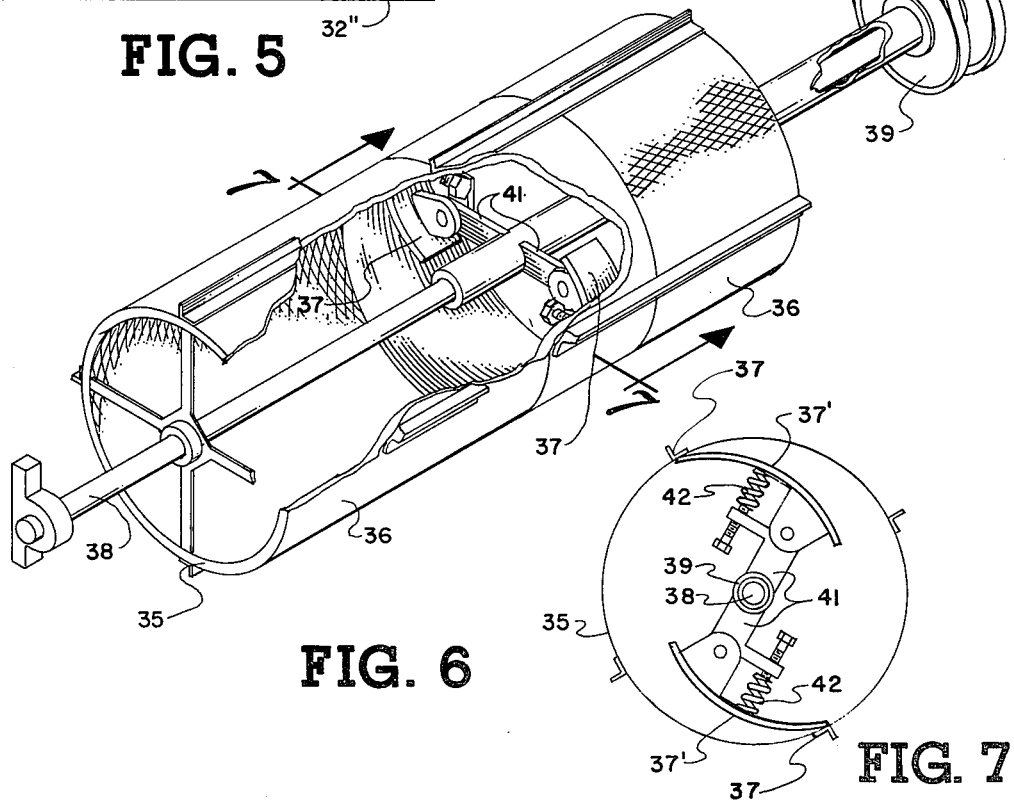
FIG. 6
FIG. 7

LEAF CUTTER BEE LARVAE EXTRACTING DEVICE

REFERENCE TO OTHER APPLICATIONS

This application is a continuation of my earlier application entitled Apparatus for Cleaning Bee Culture Frames, Ser. No. 574,079 filed May 2, 1975, now abandoned.

FIELD OF INVENTION

The present invention relates to bee culture frames, and more particularly to apparatus for removal of larvae from bee frames.

DESCRIPTION OF THE PRIOR ART

Means for removal of larvae from bee culture frames have largely been relegated to manual techniques. Such work has been expensive and unpleasant. The problems of cleaning bee culture frames designed for a specific specie, such as the leaf cutter bee, have been particularly acute. Frames for leaf cutter bees and the like require segmented structures which may either comprise boards having a multiplicity of holes or grooves. The complexity and intricacy of mechanical devices required to clean larvae from such frames is obvious.

Accordingly, it is an object of the present invention to provide apparatus for removal of larvae from segmented bee culture frames, such as the bee frames used for colonies of leaf cutter bees.

It is a further object of the present invention to provide means for separating pollen, honey and larvae removed from bee culture frames of this invention.

It is still another object of this invention to provide means for reassembling frames cleaned by the present apparatus.

These and other objects shall become apparent from the description following, it being understood that modifications may be made without affecting the teachings of the invention here set out.

SUMMARY OF THE INVENTION

The apparatus for cleaning bee culture frames of the type having slots for frames, which are formed into blocks by aligning the frames, comprises a suitable framework, an in-feed ramp, a board-breaker assembly, and a board-cleaning assembly. The infeed ramp carries the blocks to a vertically disposed channel provided on the framework, the channel providing means for controlling forward movement of the block on the ramp and providing means for conducting frames separated from the block downwardly in the apparatus. The board-breaker assembly comprises a blade reciprocating vertically in a channel disposed parallelly to the frames with the contact face of the blade being disposed at a pre-determined position to operate adjacently disposed frames in the block, and frame-cleaning teeth which interagitate with slots of the frame. The board-cleaning assembly is disposed distally below the board-breaker assembly along the vertical channel, the cleaning assembly having means for removing foreign material, larvae and the like from the frames, and a reassembly and off-feed assembly including an off-feed conveyor disposed below the cleaning assembly at the lowermost portion of the channels, the channels being provided with means rectilinearly aligning the frames into the block. The apparatus may also include a larvae separator.

A more thorough and comprehensive understanding may be had from the detailed description of the preferred embodiment when read in connection with the drawings forming a part of this specification.

BRIEF DESCRIPTION OF THE DRAWINGS

FIG. 4 is a side-elevational view of the apparatus of the FIG. 3.

FIG. 5 is an elevational view of the slot-cleaning teeth employed herein.

FIG. 6 is a fragmentary perspective view taken substantially along lines 6—6 of the FIG. 3 of the larvae separating assembly of this invention.

FIG. 7 is a cross-sectional, elevational view taken substantially along the lines 7—7 of the FIG. 6.

DETAILED DESCRIPTION OF THE PREFERRED EMBODIMENT

Figure 1:
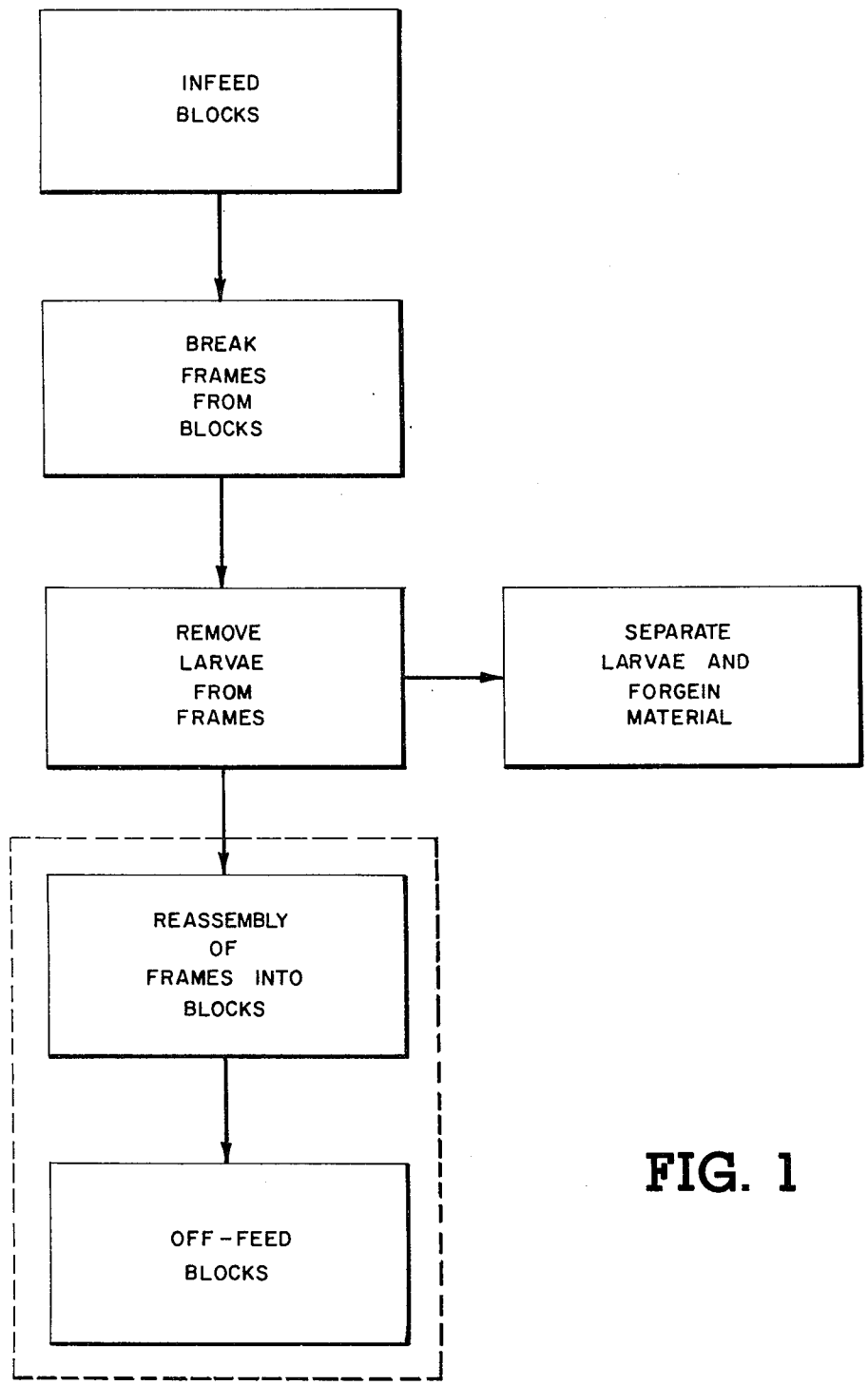
FIG. 1 is a flow chart of steps accomplished by the apparatus of this invention.

Referring now to the drawings, and more particularly to the FIG. 1, steps accomplished by the apparatus for extracting larvae from bee culture frames of this invention is shown to advantage and comprises the steps of in-feeding a block of assembled bee culture frames, breaking the frames from the assembly, removing larvae from the individual frames, reassembling the frames into blocks, and off-feeding the blocks. The apparatus of this invention may also be provided with means for separating larvae and the like removed from the bee culture frames.

Figure 2:
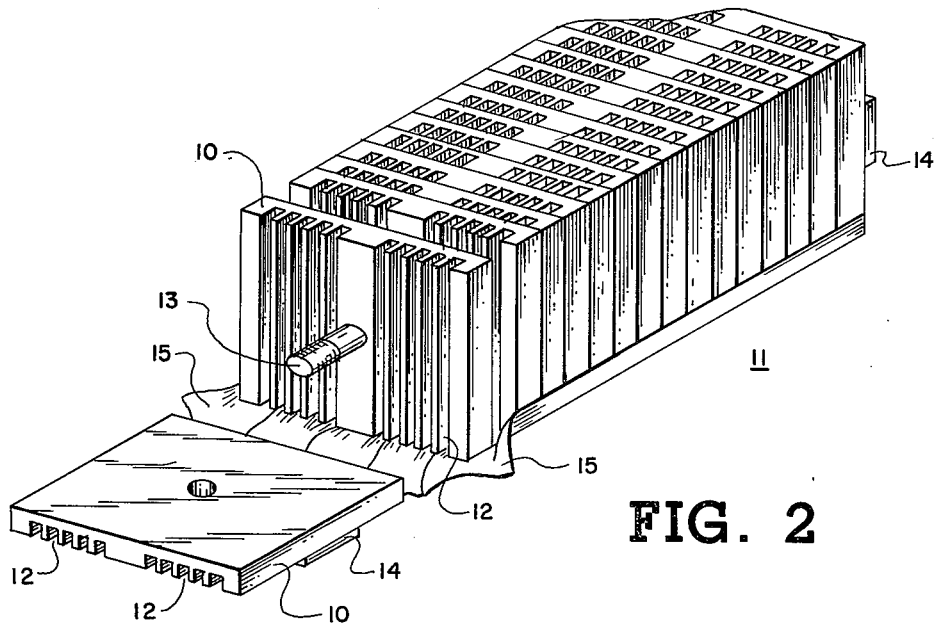
FIG. 2 is a perspective view of a typical bee culture frame especially suited for cleaning by the apparatus of this invention.

Referring to the FIG. 2, bee culture frames which are particularly adapted to be cleaned by the present apparatus are shown to advantage and generally identified by the numeral 10. The frames 10, or boards as they are known, are stacked to form a block 11 which forms a principle component of a colony. Frames, or boards, 10 shown in the FIG. 2 are particularly adapted to species such as the leaf cutter bee. Each frame or board 10 may comprise a block of wood having a multiplicity of parallelly disposed slots 12 cut into one face of the board. The block 11 is formed by placing all of the slotted faces of the boards 10 in the same direction and securing the boards in alignment by a shaft 13 having metal end plates 14 at each of its terminal ends. It has been found to advantage to close one of the faces of the block 11 which present the holes or ends of the slots 12 with tape 15. The tape 15 prevents predators from entering through and over the end of the boards 10 to attack larvae.

Figure 3:
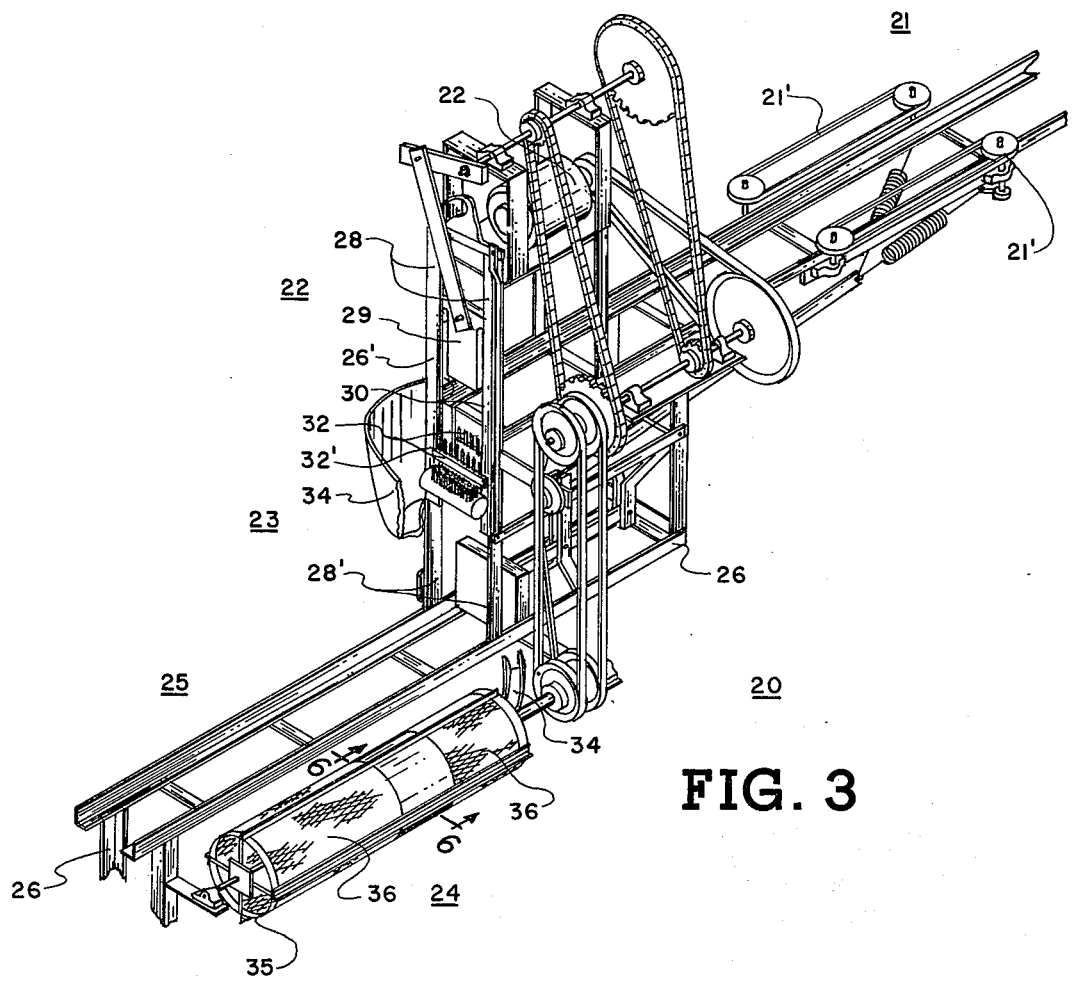
FIG. 3 is a perspective view of the apparatus of this invention.

Referring to the FIG. 3, the apparatus for extracting leaf cutter bee larvae of this invention is shown to advantage and generally identified by the numeral 20. The apparatus 20 includes an in-feed ramp or conveyor 21, a board breaking assembly 22, a board-cleaning assembly 23 which may have a material separating assembly 24, and a reassembly and off-feeding conveyor 25. The in-feed ramp 21 includes a drive assembly 21' more clearly shown in FIG. 7. It is to be understood that the apparatus 20 is supported by a suitably configured and stiffened framework 26 which also provides means supporting drive apparatus such as motors 22 and the like. It is also to be understood that material handling apparatus such as the in-feed conveyor 21 and the off-feed assembly 25 may either be fabricated as slides having suitable driving mechanisms or mechanized endless belts. In the case of the in-feed conveyor 21, it is to be understood that the framework 26 should be provided with an end stop 26' which defines the forward, horizontal travel of a block 11 being fed into the apparatus 20. This end stop 26' may be provided by an upstandingly disposed pair of channel members 28' which may engage vertically disposed edges of the bee frames or boards 10, and may travel downwardly along the channels 28. It is to be understood that drive means providing additional downwardly urging force to boards 10 broken free by the apparatus 20 may be provided to insure proper travel.

Under usual circumstances, the bee frames or boards 10 become fused together by pollen and adhesive material applied by the bees themselves. This requires that the frames or boards 10 be separated by a mechanical board-breaker assembly 22. The board-breaker assembly 22 comprises a frame-separating blade 29 which reciprocates vertically in channels 30 which are disposed adjacent with the channels 28 described above. The lowermost, frame-contacting face of the blade 29 is so configured as to engage the uppermost terminal edge of the forwardmost frame 10 in the block 11. The blade 29 may be actuated by any of a number of prime movers such as an hydraulic cylinder (not shown).

AS the blade 29 actuates each frame 10 downwardly through the channels 28, larvae and other material in the slot 12 is removed by rows of teeth 32' which are oriented transversely to and projects into the line of travel of the frame 10 defined by the channels 28. Each of the teeth 32' has a diameter substantially the same as the width as the slots 12. As shown in the FIG. 5, the teeth 32' are fixedly mounted at suitable intervals on a mounting bar 32''. The distance between the teeth 32' is sufficient to permit the teeth 32'' to interdigitate with the slots 12. It has been found to advantage to fabricate the teeth 32' with pointed ends to dislodge larvae with less damage.

In some embodiments of the frames 10, and as a result of certain ways of assembling the frames 10 into a block 11, slots 12 will appear on both sides of the frames 10. Accordingly, a row of teeth 32 may be mounted on a bracket 32'' in a manner similar to the row of teeth 32 described above. The row of teeth 32 project into the channel 28 from the side opposite the row 32 described above. Because the apparatus 20 should be adapted to handle either single or double sided slotted frames 10, it has been found to advantage to pivotally mount between springs (not shown) the row 32 on the channel 28 and to provide a projection 33 on the blade 29 to momentarily urge the teeth into a position outwardly at an angle with respect to the channel 28, and thereby align the teeth 32' with grooves 12 of the frames 10.

After a bee frame 10 has been removed from the block 11, it travels downwardly along the channels 28 and is treated by the board-cleaning assembly 23. The bee frame 10 is then permitted to travel still farther down along the channels 28. Material removed from the bee frame 10 is collected in a pan or larvae chute 34.

The separating assembly 24 permits material to be separated from the larvae and the like. Generally, the separator comprises a cylindrical drum 35 having both of its terminal ends open and its circumferential wall fabricated of an openwork material, such as wire mesh 36 and the like. As above, the drum 35 may be driven by one of the motors 22, or as shall be understood hereinafter other means agitating larvae 10, the drum 35 may be employed. The rotary drum 35 may have its central rectilinear axis canted in a downward direction such that material is discharged from the end disposed farthest from the main body of the apparatus 20.

As shown more clearly in the FIG. 6, the interior of the drum 35 is provided with pulverizing shoes 37, which serves to agitate and clear material treated in the assembly 24. The drum 35 is fastened concentrically to a shaft 38, which is journally mounted to a portion of the framework supporting the apparatus 20. The shaft 37 is provided with an overrunning sleeve which is provided with a pulley 39, which is connected by a V-belt 40 to the motor 22. The shoes 37 are pivotally mounted on radially disposed web members 41. Each of the shoes 37 have an arcuate cross section, which is disposed convexly to the interior cylindrical wall of the drum 35. The shoe 37 is fastened at one of its edges to the web 41, and is urged with the edge opposite that mounted to the web 41 against the interior wall of the drum 35 by a spring 42. Thus, as the shoes 37 are rotated on the shaft 38, the trailing edge of each shoe 37 is urged adjacent the mesh of the drum 35. It has been found to advantage to coat the drum-contacting face of the shoes 37 with an elastomeric foam material 37'.

The reassembly and off-feed assembly 25 comprises a conveyor 37 disposed distally below the cleaning assembly 23 at the end of the channel 28 is provided with exitways 28', which align the individual frames 10 to form blocks 11 of the type set out above. As with the in-feed conveyor 21, the off-feed conveyor 37 may be mechanically driven, or have secondary mechanical means urging the frames 10 and the block 11 for proper assembly.

Having thus described in detail a preferred apparatus which embodies the concepts and principles of the invention and which accomplishes the various objects, purposes and aims thereof, it is to be appreciated and will be apparent to those skilled in the art that many physical changes could be made in the apparatus without altering the inventive concepts and principles embodied therein. Hence, it is intended that the scope of the invention be limited only to the extent indicated in the appended claims.

I claim:
1. An apparatus for cleaning bee culture frames of the type having slots for frames, which are formed into blocks by aligning said frames, comprising:
   a suitable framework;
   an in-feed ramp carrying said blocks to a vertically disposed channel provided on said framework, said channel providing means for controlling forward movement of said block on said ramp and providing means for conducting frames separated from said block downwardly;
   a board-breaker assembly comprising a blade reciprocating vertically in a channel disposed parallelly to said frames with the contact face of said blade being disposed at a pre-determined position to operate at the upper edge of the forwardmost frame in said block; and
   a board-cleaning assembly disposed distally below said board-breaker assembly along said vertical channel, said cleaning assembly having means for removing larvae and the like from said frames, and a reassembly and off-feed assembly including an off-feed conveyor disposed below said cleaning assembly at the lowermost portion of said channels, said channels being provided with means rectilinearly aligning said frames into said block.

2. The apparatus of claim 1 wherein said means for removing larvae, and the like from said frames includes a row of teeth disposed transversely to and projecting into said means conducting said frames downwardly, said row of teeth being adapted to interdigitate with said slots of said frames.

3. The apparatus of claim 2 wherein a pair of rows of teeth are mounted to project from opposing sides into said means conducting said frames downwardly.

4. The apparatus of claim 3 wherein one of said pair of rows of teeth is mounted on a spring-loaded bracket, being adapted to urge said teeth into said means conducting said frames downwardly, and which is adapted to permit a frame not having slots on the side from which row of teeth mounted on said bracket projects may cam said teeth out of said means conducting said frames.

5. The apparatus of claim 1 wherein said cleaning assembly includes a larvae chute which may discharge larvae and the like sidewardly with respect to said apparatus.

6. The apparatus of claim 1 including a separating assembly comprises a drum having both of its terminal ends open and with its circumferential wall fabricated of an openwork material, and having means adapted to agitate said larvae therein.

7. The apparatus of claim 6 wherein said drum of said separating assembly is provided with shoes adapted to scrape larvae and the like from the interior side of said drum.

8. The apparatus of claim 7 wherein said shoes are provided with means for rotating said shoes relative to said drum.

9. The apparatus of claim 7 wherein the face of each of said shoes contacting the interior side of said drum is provided with an elastomeric foam coating.

* * * * *